United States Patent [19]

Loozen

[11] 4,385,056

[45] May 24, 1983

[54] BENZO[4,5]PYRANO[2,3C]PYRROLES AND PHARMACEUTICAL PREPARATIONS CONTAINING SAME

[75] Inventor: Hubert J. J. Loozen, Veghel, Netherlands

[73] Assignee: Akzo N.V., BH OSS, Netherlands

[21] Appl. No.: 311,324

[22] Filed: Oct. 14, 1981

[30] Foreign Application Priority Data

Oct. 18, 1980 [NL] Netherlands ............... 8005754

[51] Int. Cl.³ .............. A61K 31/40; A61K 491/052
[52] U.S. Cl. ................. 424/248.55; 424/248.57; 424/248.58; 424/250; 424/267; 424/273 R; 424/273 P; 424/274; 544/142; 544/373; 544/198; 546/198; 548/300; 548/336; 548/348; 548/356; 548/421; 548/430
[58] Field of Search ............ 260/326.25, 326.29, 260/326.5 B; 544/142, 373; 546/198; 548/336, 348, 300, 356, 421, 430; 424/248.55, 248.57, 248.58, 250, 267, 273 R, 273 P, 274

[56] References Cited

U.S. PATENT DOCUMENTS 3,888,946  6/1975  Pars et al. ............... 424/274 X
4,132,709  1/1979  Santroch et al. .......... 546/89

OTHER PUBLICATIONS

Chemical Abstracts Registry Index, 1973 [40635-90-3].

*Primary Examiner*—Richard Raymond
*Attorney, Agent, or Firm*—Abelman, Frayne & Rezac

[57] ABSTRACT

Benzo[4,5]pyrano[2,3c]pyrrole derivatives of the general formula:

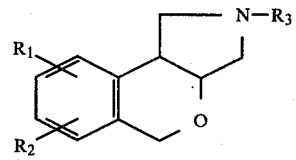

I or pharmaceutically acceptable acid addition salts thereof, in which $R_1$ and $R_2$ represent hydrogen, alkyl, alkoxy, aralkoxy, hydroxy, halogen, methylenedioxy or acyloxy, and $R_3$ represents hydrogen, alkyl, aralkyl or aminoalkyl, are potent dopamine agonists.

6 Claims, No Drawings

BENZO[4,5]PYRANO[2,3c]PYRROLES AND PHARMACEUTICAL PREPARATIONS CONTAINING SAME

The present invention relates to new benzo(4,5) pyrano(2,3c)pyrrole derivatives, to methods for preparing these compounds, and to pharmaceutical preparations containing such compounds as the active component.

More especially the invention relates to compounds having the general formula I:

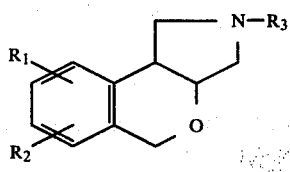

in which
$R_1$ and $R_2$ represent hydrogen, alkyl (1-6 C), alkoxy (1-6 C), aralkoxy, hydroxy, halogen, methylenedioxy or acyloxy, and
$R_3$ represents hydrogen, alkyl, aralkyl or amino-alkyl, and pharmaceutically acceptable acid addition salts thereof.

The compounds in accordance with the invention are particularly effective as dopamine-agonists.

The compounds of the invention are prepared in a manner commonly used for the preparation of analogous compounds.

A quite useful method is starting from a compound having the general formula II:

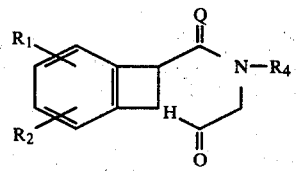

or an acid addition salt thereof, in which $R_1$ and $R_2$ have the meanings already indicated; Q represents either 2 hydrogen atoms or 1 oxygen atom, and $R_4$ has the same meaning as $R_3$, but furthermore can represent an acyl group or an alkoxycarbonyl group.

This compound II is converted thermolytically into a compound having the general formula III

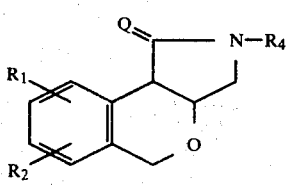

or an acid addition salt thereof, in which $R_1$, $R_2$, $R_4$ and Q have the meanings already assigned above.

Thermolysis takes place preferably at a temperature between 100° and 200° C., and more particularly at 160°-180° C.

Preferably thermolysis is applied to those compounds II, in which an amide bond is present; this means that those compounds II are the preferred starting products, in which either Q represents oxygen, or $R_4$ represents an alkoxy-carbonyl or acyl group.

The compound obtained having formula III is (insofar as this does not yet correspond with a compound in accordance with Formula I) converted in a conventional manner into a compound of formula I. Thus a compound III, in which Q represents oxygen, is reduced in a manner usually applied for the reduction of an amide group, to the corresponding compound in which Q represents hydrogen. Such reduction is preferably carried out using a complex metal hydride such as lithium aluminium hydride, or using diborane or using borohydride in dimethylsulphide and tetrahydrofuran.

A compound III in which $R_4$ represents an acyl group can be hydrolysed or reduced to a compound I. Hydrolysis to give a compound I in which $R_3$ represents hydrogen is carried out in a conventional way using a strong acid or strong base, such as concentrated HCl or a concentrated NaOH solution. An acyl group can furthermore be reduced to a compound I in which $R_3$ represents an alkyl, aralkyl or amino-alkyl group. Such reduction is carried out using the same reductive agents as already described above.

When $R_4$ in the compound of formula III represents an alkoxy-carbonyl group, a compound I in which $R_3$ represents hydrogen is obtained by hydrolysis in acid or basic milieu. Reduction of said alkoxy-carbonyl group, preferably with the aid of a complex metal hydride, gives the corresponding compound I in which $R_3$ represents methyl.

The compounds of formula II, being starting material in the present synthesis, can be prepared in a manner commonly used for the preparation of analogous compounds. In the reaction schemes of the Examples 1 and 4 more details are given, inter alia, of the preparation of these starting products.

The compounds of formula I contain 2 chiral centres, so that two racemates I (one cis- and one trans-racemate) and 4 optically active compounds I are possible. The various stereo-isomers, and or enantiomers, all belong to the compounds in accordance with the invention.

This cis- and trans compounds of formula I can be separated in the conventional manner by means of fractionated crystallisation, column chromatography, preparative thin layer chromatography or partition chromatography.

It is also possible, of course, to prepare the specific cis or trans isomer I by carrying out a cis/trans separation of an intermediate product in the synthesis of the compounds I and to convert the cis or trans intermediate obtained into the corresponding cis or trans endproduct of formula I. A particularly suitable intermediate product in this respect is a compound III, where Q represents oxygen.

A racemic compound I can be resolved in the conventional manner into its optical antipodes, for example with the aid of an optically active acid. The resolution can, however, also be carried out with the intermediate product III. In this case the synthesis described results direct into an optically active endproduct of formula I.

The acid addition salts of the compounds of the invention are prepared in the conventional manner by allowing the free base of formula I to react with an acid, such as HCl, HBr or HI, phosphoric acid, acetic acid, maleic acid, malonic acid, fumaric acid, succinic acid, tartaric acid, citric acid, ascorbic acid or salicylic acid.

Obviously it is possible to convert one compound of the invention into another compound of the present invention.

It is possible for example to alkylate or aralkylate the unsubstituted (at the nitrogen atom) amine of formula I ($R_3$ is hydrogen) in a conventional manner, e.g. by reaction with an alkyl, aralkyl or amino-alkyl-halogenide or by acylating the nitrogen atom involved and subsequently reducing the resultant N-acyl compound. The introduction of methyl groups at the nitrogen atom in question is preferably carried out in accordance with the procedure of Eschweiler-Clarke (reaction with formaldehyde and formic acid) or by using the reaction with formaldehyde and sodium cyanoborohydride in a suitable, solvent, such as acetonitrile.

Furthermore it is possible to hydrolyse an alkoxy or aralkoxy substituent, preferably a methoxy substituent, at the phenyl group to the corresponding hydroxy group, e.g. with the aid of an acid such as $BBr_3$ or HBr. A benzyloxy group can be converted into the corresponding hydroxy group by reduction in a conventional manner.

This hydroxy group can subsequently be converted in the conventional manner into an acyloxy group by reaction with the desired carboxylic acid or the acid halide, anhydride or reactive ester thereof.

The compounds of the invention exert as already said above a stimulating effect on the dopamine receptors, so that they are suitable inter alia in the prophylatic treatment of a heart infarct and in the treatment of patients suffering from Parkinson's disease.

Above all, however, the dopamine-agonists of formula I inhibit the prolactine secretion, so that they can be used in the treatment of troubles or symptoms which accompany (or are caused by) an abnormally high prolactine level. In this connection the compounds I can be used in the treatment of ovarian dysfunctions such as irregular cycles and amenorrhoea and in the treatment of pituitary tumors.

In addition the dopamine agonists of formula I can be used as contraceptives, in the treatment of hot flushes and in the treatment of patients at high risk of endometrium and breast cancer.

Compounds I can be administered both enterally and parenterally.

Mixed with suitable carriers they can be brought into a form which is suitable for oral administration such as pills, tablets and capsules. For injection purposes the compounds are dissolved, emulsified or suspended in a liquid suitable for injection.

The present compounds can furthermore be administered in the form of a suppository or spray.

The compounds of formula I are preferably administered in a daily dosage of between 0.01 mg and 20 mg per kg body weight. For human use a dosage of between 1 and 500 mg per day is recommended.

By an alkyl group in the definition of $R_1$, $R_2$ and $R_3$ is to be understood a saturated alkyl group having from 1 to 6 carbon atoms, such as methyl, ethyl, propyl, isopropyl, butyl, isobutyl, tertiary butyl, pentyl and hexyl.

By an aralkyl group in the definition of $R_1$, $R_2$ and $R_3$ is meant an alkyl group (as defined above) which is substituted with an aromatic group such as a phenyl or naphthyl group. Said aromatic group can in addition be substituted with one or more alkyl, halogen, hydroxy or alkoxy groups. The preferred aralkyl group is a substituted or unsubstituted phenyl-alkyl group having 7–12 carbon atoms, such as phenylmethyl, phenylethyl, p.hydroxy phenylethyl, m.p.dihydroxy phenylethyl, p.methoxy phenylethyl, m.p.dimethoxy phenylethyl, phenylpropyl, etc.

The alkyl and aralkyl components of the "alkoxy", "alkoxycarbonyl" and "aralkoxy" groups as used in the definitions of $R_1$, $R_2$ and $R_4$ have the same meanings as described above.

The amino-alkyl group present in the definition of $R_3$ is a group of the following formula:

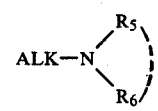

where
ALK represents an alkylene group having 1–6 carbon atoms, and
$R_5$ and $R_6$ represent hydrogen or alkyl (1–6 C) or together with the nitrogen a heterocyclic 5- or 6-ring such as pyrrole, pyrroline, pyrrolidine, piperidine, imidazole, imidazoline, imidazolidine, pyrazolidine, morpholine, N-methylpiperazine or N-phenylpiperazine.

Preferred compounds of the invention are those compounds of formula I which possess one or two oxygen-containing substituents at the benzo group ($R_1$ and/or $R_2$). Particularly preferred compounds of formula I possess a mono-alkoxy, aralkoxy, hydroxy or acyloxy substituent at one of the positions 6, 7 or 8, whereby position 8 is the most suitable, or possess a di-alkoxy, di-aralkoxy, dihydroxy, di-acyloxy or a methylenedioxy substitution pattern, at the positions 7, 8 or 6, 7.

Generally the trans compounds of formula I are more active than the corresponding cis-isomers, so that the trans-isomers of formula I are to be preferred.

The following numbering system and nomenclature have been employed for the basic structure.

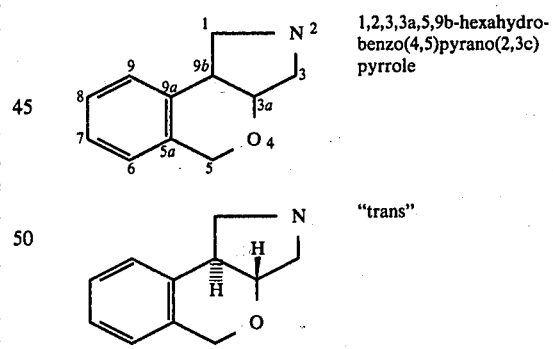

1,2,3,3a,5,9b-hexahydro-benzo(4,5)pyrano(2,3c)pyrrole

"trans"

EXAMPLE 1

Trans, 7,8-dibenzyloxy-1,2,3,3a,5,9b-hexahydro-2-(2-phenylethyl)-benzo[4,5]pyrano[2,3c]pyrrole and corresponding cis-isomer

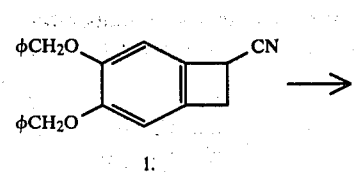

1.

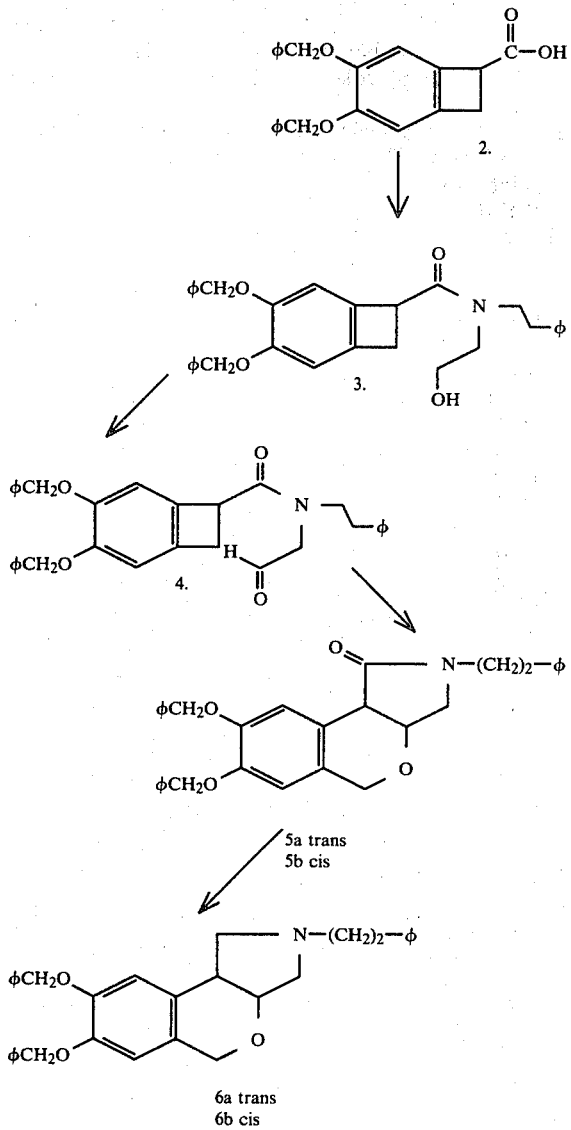

(a) A solution of 330 g KOH in 220 ml water was added to a suspension of 190 g carbonitrile 1 in 1470 ml ethanol. The mixture was refluxed for 8 hours under nitrogen atmosphere and then poured into water. After acidification of this mixture with 1 liter of 6 N HCl the mixture was extracted with ethyl acetate. The organic layer was washed with water, dried on $Na_2SO_4$, after which the solvent was evaporated. Yield 180 g 2; melting point 103°–104° C.

(b) A mixture of 14 g of the carboxylic acid 2 and 50 ml $SOCl_2$ was refluxed for one hour after which the $SOCl_2$ was evaporated. The residue was dissolved in 50 ml dry methylene chloride, after which this solution was added drop-wise to a cooled ($-50°$ C.) solution of 7 g phenylethylamino-ethanol in a mixture of 150 ml methylene chloride and 50 ml triethylamine. After being stirred for one hour at room temperature 500 ml of 2 N sulphuric acid was added to the reaction mixture. The mixture was subsequently (twice) extracted with methylene chloride, after which the organic layer was washed consecutively with a saturated $NaHCO_3$ solution and water and then dried on sodium sulphate. The solvent was then evaporated and the residue was crystallised with the aid of methylene chloride/isopropyl ether (1:1). Yield: 18 g 3; melting point 160°–161° C.

(c) The oxidation agent was prepared by adding dropwise a solution of 15 ml dimethylsulphoxide in 90 ml dry methylene chloride to a cooled solution ($-70°$ C.) of 9 ml oxalylchloride in 250 ml methylenechloride under nitrogen atmosphere. A solution of 15 g of the amino-alcohol 3 in 100 ml methylene chloride was added to this oxidation agent at $-70°$ C., after which stirring was continued for some time at this temperature. Then 50 ml of triethylamine was added drop-wise to the mixture. After heating up to room temperature and addition of 300 ml water the mixture was extracted with methylene chloride. The organic layer was washed consecutively with 2 N HCl, saturated $NaHCO_3$ solution and water, after which it was dried after which the solvent was evaporated. The oily residue was chromatographed over silicagel with toluene/ethylacetate (9:1). Yield: 12 g aldehyde 4.

(d) A solution of 10 g aldehyde 4 in 250 ml bromobenzene was refluxed under nitrogen atmosphere for 16 hours. Then the solvent was evaporated and the residue obtained was subjected to chromatographic purification above silicagel with the aid of toluene/ethylacetate (9:1). Yield: 7.0 g trans-amide 5a, melting point 134°–135° C., and 1.2 g cis-amide 5b, melting point 95°–96° C.

(e) 30 ml of a 10 ml solution of the borane-methylsulphide complex in THF was added to a solution of 20 g of the trans-amide 5a in 500 ml tetrahydrofuran (THF). The reaction mixture was then refluxed under nitrogen for 3 hours. While stirring, 100 ml of 6 N HCl was added to the reaction mixture which was then refluxed for a further 2 hours. After 1.5 liters of saturated $NaHCO_3$ solution had been added to the resultant mixture, extraction was carried out with diethylether. The organic phase was washed with water and then dried. After evaporation of the solvent the residue was chromatographed over silicagel. Yield: trans-amine 6a: 18 g, melting point 84°–86° C.

(f) In the same manner as described in (e) the cis-amide 5b was converted into the cis-amine 6b; melting point 6b: 91°–94° C.

EXAMPLE 2

Trans-1,2,3,3a,5,9b-hexahydro-2-(2-phenylethyl)benzo[4,5]pyrano[2,3c]-pyrrole-7,8-diol-acetate 900 mg of palladium (10%) on carbon was added to a solution of the trans-amine (obtained in Example 1e) in 100 ml glacial acetic acid, after which the mixture was hydrogenated.

After the mixture had taken up all hydrogen the catalyst was removed by filtration. Then the solvent (acetic acid) was evaporated off. The addition of a small amount of di-isopropylether to the residue gave 7.2 g crystalline product, melting point 185°–186° C.

EXAMPLE 3

In a manner corresponding to that described in Examples 1 and 2 the following compounds were prepared:

cis-1,2,3,3a,5-9b-hexahydro-2-(2-phenylethyl)-benzo[4,5]pyrano[2,3c]pyrrole-7,8-diol; melting point 154°–156° C.;

cis-7,8-dimethoxy-1,2,3,3a,5,9b-hexahydro-2-methyl-benzo[4,5]pyrano[2,3c]pyrrole;

trans-7,8-dimethoxy-1,2,3,3a,5,9b-hexahydro-2-methyl-benzo[4,5]pyrano[2,3c]pyrrole; melting point 91°–92° C.;

cis-7,8-dimethoxy-1,2,3,3a,5,9b-hexahydro-2-propyl-benzo[4,5]pyrano[2,3c]pyrrole;

trans-7,8-dimethoxy-1,2,3,3a,5,9b-hexahydro-2-propyl-benzo[4,5]pyrano[2,3c]pyrrole.HCl; melting point: 226°–228° C.;

cis-7,8-dibenzyloxy-1,2,3,3a,5,9b-hexahydro-2-benzyl-benzo[4,5]pyrano[2,3c]pyrrole; melting point: 86°–88° C.;

trans-7,8-dibenzyloxy-1,2,3,3a,5,9b-hexahydro-2-benzyl-benzo[4,5]pyrano[2,3c]pyrrole; melting point: 94°–95° C.;

trans-7,8-dibenzyloxy-1,2,3,3a,5,9b-hexahydro-2-propyl-benzo[4,5]pyrano[2,3c]pyrrole; melting point HCl salt: 212° C.;

cis-1,2,3,3a,5,9b-hexahydro-8-methoxy-2-methyl-benzo[4,5]pyrano[2,3c]pyrrole.HCl, melting point: 209° C.; and the corresponding trans-isomer.HCl, melting point: 214° C.;

cis-1,2,3,3a,5,9b-hexahydro-benzo[4,5]pyrano[2,3c]pyrrole-7,8-diol.acetate; melting point: 225°–227° C.;

trans-1,2,3,3a,5,9b-hexahydro-benzo[4,5]pyrano[2,3c]pyrrole; 7,8-diol.acetate; melting point: 181°–183° C.;

cis-1,2,3,3a,5,9b-hexahydro-2-methyl-benzo[4,5]pyrano[2,3c]pyrrole-7,8-diol; melting point 180° C. (dec.);

trans-1,2,3,3a,5,9b-hexahydro-2-methyl-benzo[4,5]pyrano[2,3c]pyrrole-7,8-diol; melting point: 222°–223° C.;

cis-1,2,3,3a,5,9b-hexahydro-2-propyl-benzo[4,5]pyrano[2,3c]pyrrole-7,8-diol; melting point: 175°–177° C.;

trans-1,2,3,3a,5,9b-hexahydro-2-propyl-benzo[4,5]pyrano[2,3c]pyrrole-7,8-diol.acetate; melting point: 138°–140° C.;

1,2,3,3a,5,9b-hexahydro-2-(m.p.dimethoxyphenyl)-benzo[4,5]pyrano[2,3c]-7,8-diol.acetate; cis-form melting point 163°–166° C. trans-form melting point 174°–176° C.

cis-1,2,3,3a,5,9b-hexahydro-2-methyl-benzo[4,5]pyrano[2,3c]pyrrole-7-ol, melting point HCl salt: 223° C., and corresponding trans-isomer, melting point HCl salt: 295° C.;

cis-1,2,3,3a,5,9b-hexahydro-2-methyl-benzo[4,5]pyrano[2,3c]pyrrole-8-ol.HCl; melting point: 211° C., and corresponding trans-isomer, melting point HCl salt: 215° C.;

cis-1,2,3,3a,5,9b-hexahydro-2-methyl-benzo[4,5]pyrano[2,3c]pyrrole-6,7-diol.HCl, melting point: 260° C.; and corresponding trans-isomer;

1,2,3,3a,5,9b-hexahydro-2-(m.p.dihydroxyphenyl)-benzo[4,5]pyrano[2,3c]-7,8-diol.acetate; cis-form melting point 140° C. (dec.) trans-form melting point 142° C. (dec.).

EXAMPLE 4

7,8-dimethoxy-1,2,3,3a,5,9b-hexahydro-benzo[4,5]pyrano[2,3c]pyrrole

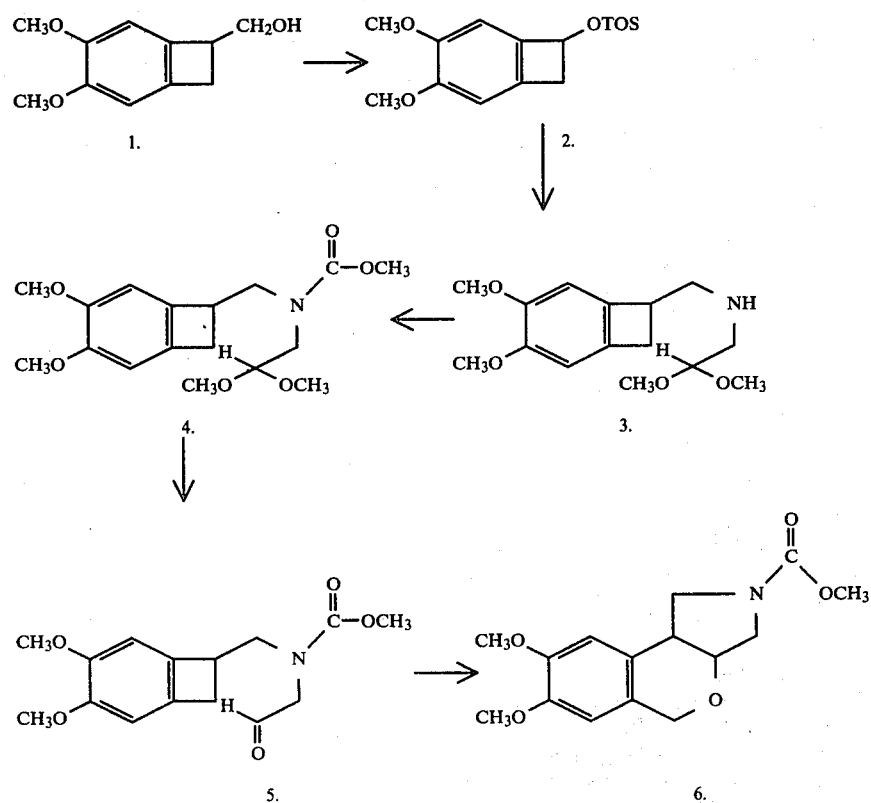

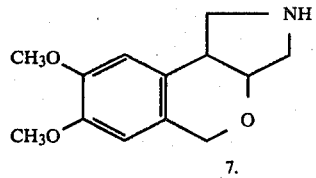

(a) A mixture of the alcohol 1, 12.5 g tosyl chloride and 100 ml pyridine was stirred for 5 hours, after which 500 ml of ice water was added. The mixture was extracted with ether. The organic layer was washed consecutively with 2 N HCl, 10% NaHCO₃ solution and water. After drying and evaporation of the solvent the oil 2 was obtained (10.5 g).

(b) A solution of the tosylate 2 in 20 ml aminoacetaldehyde-dimethylacetal was heated for 16 hours at a temperature of 100° C. The mixture was then poured into 200 ml in a 10% NaHCO₃ solution, after which it was extracted with methylene chloride. The organic fraction was dried and concentrated after which the residue (oil) was subjected to chromatography over silicagel using methylene chloride/methanol (96:4) as running agent. Yield 7.6 g oil 3.

(c) 10 ml triethylamine was added to a solution of 7.4 g of the amine 3 in 100 ml ether. Then 2.2 ml of methylchloroformate was added drop-wise at 0°–5° C. and stirred. After the mixture had been diluted with icewater it was extracted with ethyl acetate. The organic layer was washed, dried and concentrated. Yield: 8.3 g oil 4.

(d) 50 ml of water was added to a solution of 8 g of the carbamate 4 in 75 ml dioxane, followed by 5 ml 70% HClO₄. The mixture was stirred for 10 hours and then neutralised by adding 300 ml of 10% sodium bicarbonate solution.

After saturation of the mixture with NaCl, it was extracted with methylene chloride. The organic layer was washed with a saturated NaCl solution and then dried and concentrated. After chromatographyical purification of the residue over silicagel with the aid of methylene chloride/5% ethylacetate, 4.5 gram of the aldehyde 5 was obtained as a colourless oil;

(e) A solution of 4.4 g of the aldehyde 5 in 20 ml bromobenzene was heated under nitrogen for 24 hours with reflux cooling. Then the solvent was evaporated. The residue was crystallised with the aid of ether. In this way 1.8 g trans product 6 was obtained, melting point 151°–153° C.;

(f) A solution of 1 g of the trans carbamate 6 in 20 ml 80% ethanol, to which 2 g KOH had been added, was boiled for 5 hours under reflux. A part of the solvent was then evaporated and the residue was treated with 40 ml water. The mixture was then extracted with methylene chloride, after which the organic layer was washed, dried and concentrated. After treatment with methanol/HCl, 450 mg of the HCl salt of 7 was obtained (trans configuration); melting point 218°–219° C.

EXAMPLE 5

7,8-dimethoxy-1,2,3,3a,5,9b-hexahydro-2-methyl-benzo[4,5]pyrano[2,3c]pyrrole

A solution of 4 g trans-7,8-dimethoxy-1,2,3,3a,5,9b-hexahydro-2-methoxycarbonyl-benzo[4,5]pyrano[2,3c-]pyrrole in THF (Example 4e) was added to a solution of 500 mg LiAlH₄ in 20 ml dry THF. The mixture was boiled for one hour after which the following were added consecutively: 0.5 ml water, 0.5 ml 20% NaOH and 1.5 ml water. After filtering off the inorganic precipitate which had formed and evaporation of the solvent a crystalline product was obtained (3.3 g) having a melting point of 91°–92° C. (trans-isomer).

EXAMPLE 6

Trans-7,8-dimethoxy-1,2,3,3a,5,9b-hexahydro-2-propyl-benzo[4,5]pyrano[2,3c]pyrrole.HCl 40 ml propionic acid was added to 4.4 g trans-7,8-dimethoxy-1,2,3,3a,5,9b-hexahydro-benzo[4,5-]pyrano[2,3c]pyrrole (Example 4f), after which the mixture was heated at 50°–55° C. Over a period of half an hour 4 g sodium borohydride was added to the solution obtained, in small portions, whereupon the mixture was stirred for a further 16 hours at 50°–55° C. Then 200 ml water was added to the reaction mixture followed by so much 5 N NaOH that the pH of the mixture was 10.

The alkaline mixture was extracted with methylene chloride, after which the organic layer was washed, dried and concentrated. This resulted in 3.9 g of a viscous oil; melting point HCl salt 226°–228° C.

EXAMPLE 7

The following compounds were prepared in a manner corresponding to that described in Examples 5 and 6:

cis-7,8-dimethoxy-1,2,3,3a,5,9b-hexahydro-2-propyl-benzo[4,5]pyrano[2,3c]pyrrole;

cis/trans-7,8-dimethoxy-2-dimethylaminoethyl-1,2,3,3a,5,9b-hexahydro-benzo[4,5]pyrano[2,3c]pyrrole.

EXAMPLE 8

Trans-7,8-dibenzoyloxy-1,2,3,3a,5,9b-hexahydro-2-methyl-benzo[4,5]pyrano[2,3c]pyrrole.HCl 4,4 g trans-7,8-dihydroxy-1,2,3,3a,5,9b-hexahydro-2-methyl-benzo[4,5]pyrano[2,3c]pyrrole was dissolved in 40 ml dry pyridine after which 5 ml of benzoyl-chloride was added.

The reaction mixture was stirred for 5 hours and then poured into 200 ml water. The mixture was subsequently extracted with ether after which the organic layer was washed consecutively with 2 N NaOH (twice) and water (twice). The residue obtained after drying and concentration of the organic layer was treated with isopropanol/HCl. Yield 8.1 g, melting point 248°–251° C.

EXAMPLE 9

The following compound was prepared in a manner corresponding to that already described for Example 8: trans-7,8-diacetoxy-1,2,3,3a,5,9b-hexahydro-2-methyl-benzo[4,5]pyrano[2,3c]pyrrole; melting point 103°–105° C.

I claim:

1. Benzo[4,5]pyrano[2,3c]pyrrole derivatives of the general formula:

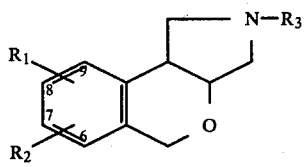

or pharmaceutically acceptable acid addition salts thereof, in which $R_1$ and $R_2$ represent hydrogen, alkyl, alkoxy, aralkoxy, hydroxy, halogen, methylenedioxy or acyloxy, and $R_3$ represents hydrogen, alkyl, aralkyl or aminoalkyl.

2. Compound as in claim 1, characterised in that $R_1$ and/or $R_2$ represent an oxygen-containing substituent.

3. Compound as in claim 2, characterised in that this oxygen-containing group is present in one of the positions 6, 7 or 8.

4. Compound as claimed in claim 2, characterised in that two oxygen-containing substituents are present in adjacent positions, either in the positions 6/7 or in the positions 7/8.

5. Compounds according to claim 1 having trans-configuration.

6. A pharmaceutical composition, useful as a dopamine agonist, containing as active ingredient an anti-dopamine effective amount of a compound according to claim 1 in a pharmaceutically acceptable carrier.

* * * * *